United States Patent [19] [11] 4,041,098
Loveless [45] Aug. 9, 1977

[54] METHOD FOR THE OLIGOMERIZATION OF ALPHA-OLEFINS

[75] Inventor: Frederick C. Loveless, Cheshire, Conn.

[73] Assignee: Uniroyal, Inc., New York, N.Y.

[21] Appl. No.: 632,342

[22] Filed: Nov. 17, 1975

Related U.S. Application Data

[63] Continuation-in-part of Ser. No. 484,836, July 1, 1975, abandoned.

[51] Int. Cl.$^2$ .......................... C07C 3/10; B01J 31/12
[52] U.S. Cl. ..................... 260/683.15 D; 252/431 R
[58] Field of Search ............................ 260/683.15 D; 252/431 R

[56] References Cited

U.S. PATENT DOCUMENTS

| | | | |
|---|---|---|---|
| 2,969,408 | 1/1961 | Nowlin et al. | 260/683.15 D |
| 3,312,748 | 4/1967 | Johnson | 260/671 |
| 3,413,376 | 11/1968 | Cleary | 260/683.15 D |
| 3,655,808 | 4/1972 | Driscoll | 260/683.15 D |
| 3,737,476 | 6/1973 | Bailly | 260/683.15 D |

*Primary Examiner*—Floyd D. Higel
*Attorney, Agent, or Firm*—Bruce F. Jacobs

[57] ABSTRACT

1. A method of oligomerizing straight chain alpha olefins having at least 3 carbon atoms comprising, generating in situ a soluble catalyst system by simultaneously adding with stirring to a reactor having an inert atmosphere and a temperature up to 200° C., a first feed comprising a straight chain alpha-olefin monomer having at least 3 carbon atoms and a minor amount of a soluble aluminum alkyl halide and a second feed comprising a straight chain alpha-olefin monomer having at least three carbon atoms and a minor amount of a soluble organic halide; wherein said soluble aluminum alkyl halide compound is selected from the group consisting of ethyl aluminum sesqui-chloride, ethyl aluminum dichloride and diethyl aluminum chloride, and said soluble organic halide is selected from the group consisting of a primary, secondary or tertiary aliphatic halide, an allylic halide or a benzylic halide, said soluble organic halide possessing; (a) at least one halogen-bearing carbon atom in the molecule and (b) not more than one halogen atom attached to any single carbon atom in said molecule; said aluminum alkyl halide being present in said catalyst system in an amount of at least about 0.1% by weight of the total monomer content and in sufficient amount to provide a total Hal/Al ratio in said catalyst system of at least about 2.5/1.

9 Claims, No Drawings

METHOD FOR THE OLIGOMERIZATION OF ALPHA-OLEFINS

This application is a continuation-in-part of application Ser. No. 484,836 filed July 1, 1975, now abandoned.

This invention relates to a novel catalyst system for oligomerizing alpha-oleins and the process in which this catalyst system is used to obtain lubricating oils, hydraulic fluids and the like, which are particularly useful at low temperature.

It is known to prepare polymeric lubricating oils by contacting an alpha-olefin with a metal halide catalyst such as $AlCl_3$ and limiting the extent of polymerization to between about 10 and 20 percent conversion of monomer to polymer as disclosed in U.S. Pat. No. 2,559,984. In the process disclosed in this patent, the reaction temperature can vary between about $-20°$ and $40°$ C. However, if conversion of the alpha-olefin is greater than about 20%, the resultant product has a poor viscosity index and pour point.

It is also known to obtain synthetic lubricating oils by contacting one or more alpha-olefins of $C_6$-$C_{14}$ range at a temperature of about $0°$ to $50°$ C. with a catalyst system formed from three types of components: (a) aluminum alkyl sesquichloride, aluminum dialkyl monochloride or aluminum monoalkyl dichloride, (b) titanium tetrachloride, and (c) an oxygen-containing organic compound which is either an oxirane or a methyl allyl ether. Such a process is disclosed in U.S. Pat. No. 3,206,523.

U.S. Pat. No. 3,179,711 discloses a similar but modified method wherein the third component in the catalyst system is tetra-alkyl silicate, in which the alkyl groups each have 1-4 carbon atoms and are unbranched, rather than an oxygen-containing hydrocarbon compound.

The preparation of synthetic lubricating oils by polymerizing an alpha-olefin with $AlCl_3$ at $57°$ C. has also been revealed to produce, e.g., a polyoctene having a viscosity index of 104 and a pour point of $-20°$ F. (*Industrial and Engineering Chemistry*, Vol. 23, No. 6, June, 1931, pp. 604–611.)

A method for producing lubricating oils by treating a petroleum distillate containing a high percentage of unsaturated hydrocarbons in the presence of $AlCl_3$ at a temperature of between $300°$ and $400°$ F. has also been disclosed in U.S. Pat. No. 1,309,432.

Thus, alpha-olefins of $C_3$ to $C_{14}$ and higher such as propene, butene, pentene, hexene, heptene, octene, nonene, decene, undecene, dodecene, tridecene and tetradecene can be oligomerized to produce oils useful as lubricants, hydraulic fluids, and the like. Hydrocarbon fractions boiling lower than about $750°$ F. are undesirable since such an aligomer has too low a flash point. Normally, hydrocarbons below $C_{20}$ are too volatile for inclusion in the products of this invention. In the oligomerization of olefins, therefore, it is desirable to convert monomers to that degree of polymerization wherein the molecular weight of the oligomer is at least equal to the molecular weight of $C_{20}$. Conversely, if the degree of polymerization is too high giving a large amount of product greater than $C_{60}$, the pour point of the resultant oligomeric mixture is generally too high to have utility.

It would be advantageous, therefore, to be able to convert alpha-olefins to a mixture of oligomers which are mainly in the $C_{20}$-$C_{60}$ range. Hydrocarbon fractions boiling below $C_{20}$ can be removed by distillation and, optionally, the premium material ($C_{20}$-$C_{60}$) may be distilled from the higher boiling moieties. However, this latter step is costly and difficult because of the high boiling points of the desired material. Thus, any process which gives good conversion of alpha-olefins to a product greater than $C_{20}$ but minimizes formation of product greater than $C_{60}$ is highly desirable. The actual amount of high molecular weight material allowed depends on the pour point desired in the end product after removal of the lower boiling hydrocarbons. Regardless of the alpha-olefin employed, higher molecular weight oligomers have greater viscosities and higher pour points. A pour point as low as $-65°$ F. is frequently desired for low temperature utilization of the product fluids.

Another important property necessary in such hydrocarbon oils is a high viscosity index (V.I.), since this means that the viscosity of the oil in question will not change significantly with temperature. In general, a viscosity index of more than 100 is very desirable.

In accordance with the present invention, synthetic lubricating oils are prepared by oligomerizing alpha-olefin utilizing a novel, soluble catalyst system. The resulting product is characterized as having a viscosity index greater than 100, a low pour point and good oxidative stability. Some of the advantages that the process of this invention exhibits over prior art processes are: more rapaid rate of reaction; cooling is not necessary and, in fact, high temperatures are beneficial; no solvent other than the alpha-olefin is required: high conversion of monomer to oligomer, and the final product does not contain an undesirable amount of high molecular weight species. It is significant to note that both components comprising the catalyst system of the invention are soluble in the monomer; i.e., the alpha-olefin. Thus, premium oligomers can be readily and continuously prepared according to the invention process by combining solutions of an aluminum alkyl halide, e.g., ethyl aluminum sesquichloride, and an organo halide, e.g., t-butyl chloride, in an alpha-olefin at elevated temperatures.

Accordingly, synthetic lubricating oils are prepared by contacting one or more straight chain alpha-olefins of $C_3$ and higher at a temperature range of up to about $200°$ C., preferably about $100°$ to $150°$ C., with a soluble catalyst system consisting of an aluminum alkyl halide and an organo halide.

The alpha-olefins which can be used in the invention process include those straight chain compounds previously mentioned, i.e., propene, butene, pentene, hexene, heptene, octene, nonene, decene, undecene, dodecene, tridecene and tetradecene.

The aluminum-containing component of the catalyst system can be either alkyl aluminum sesquichloride ($R_3Al_2Cl_3$), a dialkyl monochloride ($R_2AlCl$), or an alkyl dichloride ($RAlCl_2$) with the alkyl group represented by R being a lower alkyl, typically one containing about 1 to 4 carbon atoms.

The organo halides operable in the invention are those containing at least one saturaated carbon atom with one halogen atom thereon. The halides may be aliphatic or benzylic. Typical of such halides are butyl bromide, t-butyl chloride, allyl iodide, methallyl chloride, benzyl bromide, 1,2-dichloroethane, propylchloride, pentyl iodide, 2,3-dichlorooctane, 2,3-dibromooctane, crotylchloride, cyclohexyl, chloride, cyclohexyl bromide, dodecyl iodide, 1-chloro eicosane, 3-chloro eicosane, 1,2-dibromohexadecane, dodecyl benzyl chloride, 1,2,7,8-tetra bromooctane, as well as mixtures of such halides. As can be seen from the above typical halides, they may have from 1 to about 30 carbon atoms or more, the halide can be chlorine, bromine or iodine, and at least one saturated carbon atom in said organo halide molecule must have on it only one halogen atom and insert therefor —per carbon atom. A multiplicity of halogen bearing carbon atoms may be present in the molecule, however not more than one halogen atom is attached to any single carbon atom in the molecule.

A particularly advantageous source of organo halide results from the halogenation of $C_{24}$ and lower fraction olefins produced as part of the oligomerization process. Such low boiling olefin by-products must be removed from the product oil in order to reduce its volatility. Halogenation of these materials produces not only an efficient organ halide cocatalyst but permits recycling of part of or all of the by-product low boiling olefins.

A convenient procedure for carrying out the invention is to dissolve the aluminum alkyl halide compound in an alpha-olefin and combine it with a solution of organo halide compound also in the alpha-olefin. The combining can take place, for example, in a heated stirred autoclave or a pipe reactor. Reactor to form the product is essentially instantaneous when the temperature is maintained at least 100° C. Depending on temperature, catalyst concentration and rate of combination, an alpha-olefin can be converted to very high yields of premium oligomer, i.e., oligomer yields of at least 50%. A premium oligomer is considered to be the $C_{20}$ through $C_{60}$ moieties as such a product exhibits optimum viscosity indexes and low pour points coupled with a high flash point. The product obtained, after removal of residual moieties lower than 20 carbon atoms, is useful as a low pour point oil without further distillation, since formation of "heavy ends"; i.e., moieties higher than $C_{60}$, can be substantially minimized by the use of this procedure. The product may optionally be hydrogenated before use for added thermal-oxidative stability.

Typically, the oligomerization can be readily carried out using three reservoirs such as reservoirs A, B and C. For example, reservoir A can contain about a 1% solution of an aluminum alkyl halide in dry alpha-olefin, reservior B can contain about a 1% solution of an organo halide in dry alpha-olefin and reservoir C is the stirred reactor. The contents of A and B are fed at a continuous rate into reactor C which is pre-heated to, preferably, at least 100° C. Optionally, reservoirs A and B can also be pre-heated. Depending on the size of reservoirs A, B and C, the rate of addition may be varied without encountering an uncontrollable temperature rise. Thus, if A and B each contains 50 pounds of alpha-olefin, a convenient feed rate is 1.5 lbs per minute from each reservoir A and B. Some temperature rise will be evidenced in C and, if undesirably high, it can be controlled by cooling C or removing the reacting mass in a continuous fashion. Usually, however, reactor C remains at a reasonable temperature and pressure so that all of A and B can be added in 20–30 minutes or less. A few minutes after A and B have been completely added, the reaction is complete and the mixture can be cooled and short-stopped by adding water. Catalyst residues are then removed by a water washing.

It is advantageous at this point in the process to pass the slightly viscous reaction product through a filtering column, such as a column of activated alumina, to remove the last catalyst traces and residual water. The product is then analyzed by gas liquid chromatography (G.L.C.) to ascertain molecular weight distribution and the amount of residual monomer and dimer. Monomer is conveniently removed at atmospheric pressure or, optionally, by steam distillation. The residue is then subjected to vacuum distillation to remove everything of lower molecular weight than about 280. Usually, removal of all products boiling at less than 150° C. at 0.1 mm Hg. insures a flash point in the product oil of not lower than about 450° F. The product oil is then again analyzed for molecular weight distribution.

Under these process conditions, alpha-olefins can be converted to up to about 90% oligomerized product oil having good pour point and viscosity index. The oligomerized product can optionally be treated with antioxidants or hydrogenated (since there is about one double bond per molecule) to improve even more its already excellent thermal-oxidative stability.

The invention is further illustrated by and will become more clear from a consideration of the following examples which are not intended to, and should not be construed as, limiting the scope of the invention. As set forth in the Examples and as used throughout the application and claims, the term "Hal/Al" denotes the ratio of the total moles of halogen in both the organo halide compound and the aluminum alkyl compound to the total moles of aluminum.

In the practice of this invention, the aluminum alkyl halide compound should be present in the catalyst system in an amount of at least about 0.1% by weight of the total catalyst system to provide a minimum Hal/Al ratio of about 2.5/1. Consistent with these minimum, operable conditions, there is no upper limit on the amount of either catalyst compound thaat can be used, but for purposes of economy the Hal/Al ratio should not exceed 25/1.

EXAMPLE I

This example demonstrates the preparation of polyoctene oil; that is, the oligomerized product oil prior to distillation.

A dry, nitrogen filled, 4-necked, 500 ml round bottom flask was fitted with (1) a y-tube holding one 125 ml dropping funnel and a water cooled condenser, (2) another 125 ml dropping funnel, (3) a thermometer and (4) a stirrer. A T-tube was inserted in the top of the water cooled condenser and nitrogen was fed through the condenser to maintain an inert atmosphere in the reaction flask. Excess nitrogen not required to maintain a partial pressure in the reaction flask was fed into a vessel containing mineral oil. The flask was immersed in an oil bath which was heated to 135°–140° C. and allowed to warm up. Then into one of the dropping funnels there was placed 100 ml of octene-1 (pre-dried by passing it through an activated alumina filtering column) and 7.5 ml of a 25% solution of ethyl aluminum sesquichloride in hexane to provide an Hal/Al ratio of 3/1. Into the other dropping funnel there was placed 100 m of dry octene-1 and 3 ml benzyl chloride. The stirrer was started and the two solutions added simultaneously at identical rates so that both solutions were added in eleven minutes. The temperature in the flask rose above that of the heating bath, which was then acting as a temperature regulator. The record of oil bath temperature and reaction mix temperature is tabulated below:

| Time (min) | Temperature, °C Flask | Oil Bath | Total Octene-1 in Flask (ml) |
| --- | --- | --- | --- |
| 0 | 116 | 135 | 0 |
| 2 | 144 | 135 | 20 |
| 5 | 148 | 137 | 80 |
| 8 | 151 | 139 | 130 |
| 11 | 151.5 | 140.5 | 200 (addition complete) |

At this point, a sample was removed from the flask and quenched in water. The sample, on analysis by gas liquid chromatography (G.L.C.), was found to have the following molecular weight distribution:

| Wt. % | | | | | | |
| --- | --- | --- | --- | --- | --- | --- |
| $C_8$ | $C_{16}$ | $C_{24}$ | $C_{32}$ | $C_{40}$ | $C_{48}$ | $C_{56}+$ |
| 1.36 | 7.41 | 12.59 | 19.88 | 22.1 | 18.15 | 18.52 |

The reaction mixture was permitted to stir in the heated bath for an additional 50 minutes and was then quenched with water. At this time the temperature in the flask was 133° C. while the temperature of the bath was 130° C. A sample, when analyzed by G.L.C., had the following molecular weight distribution:

| Wt. % | | | | | | |
| --- | --- | --- | --- | --- | --- | --- |
| $C_8$ | $C_{16}$ | $C_{24}$ | $C_{32}$ | $C_{40}$ | $C_{48}$ | $C_{56}+$ |
| 0.64 | 9.49 | 14.10 | 19.49 | 19.36 | 14.10 | 22.82 |

This example illustrates that octene-1 can be rapidly converted to oligomeric materials in a very short period of time and at high yields; in this instance, 90% oligomer. The temperature record reveals that no dangerous "runaway" exotherms are encountered in the process.

Since the molecular weight distributions of samples taken immediately after mixing was complete and 50 minutes later were nearly identical, it establishes that under these conditions, not only is the rate of reaction extremely rapid, almost instantaneous, but that there is essentially no change in the oligomeric product by permitting additional time in the reactor after addition is completed.

EXAMPLE II

This example was carried out in the same manner as Example I using the same ingredients and amounts except that the two octene solutions were mixed over a period of 31 minutes. Again, the time-temperature record shown below reveals that the reaction was readily controllable.

| Time (min) | Temperature °C Flask | Bath | Total Octene-1 in Flask (ml) |
| --- | --- | --- | --- |
| 0 | 123 | 141 | 0 |
| 9 | 142 | 145 | 75 |
| 22 | 150 | 150 | 125 |
| 31 | 147 | 145 | 200 (addition complete) |

Samples taken at 31 minutes and 60 minutes were analyzed as before by G.L.C. and had the following molecular weight distribution:

| | Wt. % | | | | | | |
| --- | --- | --- | --- | --- | --- | --- | --- |
| | $C_8$ | $C_{16}$ | $C_{24}$ | $C_{32}$ | $C_{40}$ | $C_{48}$ | $C_{56}+$ |
| 31' | 7.70 | 9.14 | 13.19 | 17.49 | 17.89 | 13.71 | 20.89 |
| 60' | 4.79 | 9.46 | 13.99 | 18.26 | 18.52 | 12.05 | 22.93 |

As can be seen, additional reaction time after addition was completed caused essentially no change in the molecular weight distribution of the whole oil obtained.

EXAMPLE III

In this example, a series of runs were made to illustrate the effect of reaction temperature on the molecular weight distribution of the oligomerized product oil. All runs were made in equipment identical to that disclosed in Example I. For each run, 6.0 ml of ethyl aluminum sesquichloride were dissolved in 100 ml dry octene-1 and 1.4 ml of t-butyl chloride were dissolved in 100 ml octene-1 to provide an Hal/Al ratio of about 3/1. These two solutions were combined over a 15 minute period into the reaction flask which was immersed in an oil bath at the recorded temperature. At the end of the 15 minute period, the reactions were quenched in the usual manner with water and analyzed by gas liquid chromatography (G.L.C.). The temperature conditions and G.L.C. results are tabulated below:

| Run | Temperature (° C.) Bath | Flask | Wt. % $C_8$ | $C_{16}$ | $C_{20}$ | $C_{24}$ | $C_{32}$ | $C_{40}$ | $C_{48}$ | $C_{56}+$ |
| --- | --- | --- | --- | --- | --- | --- | --- | --- | --- | --- |
| A | 23.5 | 23–73 | 19.0 | 1.3 | 0.9 | 5.8 | 5.5 | 9.4 | 8.1 | 50.0 |
| B | 41 | 36–70 | 20.1 | 1.1 | 1.0 | 5.5 | 5.1 | 8.8 | 7.7 | 50.8 |
| C | 60 | 50–89 | 17.6 | 1.6 | 1.1 | 7.2 | 7.7 | 11.1 | 9.8 | 44.0 |
| D | 80 | 72–95 | 18.6 | 1.9 | 1.0 | 8.8 | 8.6 | 12.3 | 10.5 | 38.2 |
| E | 105 | 93–115 | 22.7 | 3.0 | 1.2 | 11.9 | 10.9 | 12.9 | 9.3 | 28.1 |
| F | 115 | 109–131 | 15.7 | 7.5 | 1.7 | 16.1 | 17.5 | 14.9 | 9.2 | 17.6 |

The above data clearly show that as the temperature of reaction is increased, monomer conversion remains essentially unchanged, but the molecular weight of the oligomerized product oil progressively decreases. This is pointed out most dramatically by comparing reaction temperature with the percent of heavy ends ($C_{56}+$) obtained. Thus, high reaction temperatures are preferred in the invention process.

EXAMPLE IV

This example is identical to Example I including ingredients and amounts thereof, except that the bath temperature in this experiment was 103° C. at the start and the solutions were added in 10 minutes. The reaction mixture was allowed to stir in the bath for an additional 50 minutes at which time it was quenched with water. The reaction condition during the run are shown below

| Time  | Temperature, ° C. | | Total Octene-1 |
|-------|-------------------|------|----------------|
| (min) | Flask | Bath | Added (ml) |
| 0  | 94  | 103 | 0 |
| 4  | 137 | 103 | 80 |
| 6  | 135 | 106 | 120 |
| 10 | 128 | 110 | 200 (addition complete) |
| 60 | 99  | 103 | |

A sample of the product taken at the end of 60 minutes revealed the following excellent molecular weight distribution by G.L.C.:

| | | | Wt. % | | | |
|---|---|---|---|---|---|---|
| $C_8$ | $C_{16}$ | $C_{24}$ | $C_{32}$ | $C_{40}$ | $C_{48}$ | $C_{56}+$ |
| 0.5 | 9.7 | 18.23 | 24.65 | 21.05 | 13.99 | 11.81 |

The product $C_{24}$ and higher, through removal by distillation of $C_8$ and $C_{16}$ moieties, was of sufficient low molecular weight; that is, less than 550, and the pour point was $-75°$ F. The 90% yield obtained in the example, in addition to obtaining a good pour point, is considerably higher than has been disclosed in prior art practices.

EXAMPLE V

This example demonstrates that the level of catalyst employed is not critical. In fact, under the conditions at which the experiments A, B and C below were run, experiment A, which contained the lowest catalyst level, produced the best product. Each experiment was carried out as described below.

Using the same apparatus as in Example I, 200 ml of octene-1 were placed in a 500 ml round bottom flask and the specified amount of ethyl aluminum sesquichloride (EASC) was then added to the octene. The solution was heated to approximately 100° C. by immersion in an oil bath. The specified amount of tertiary butyl chloride (t-BuCl) was then added dropwise over a period of 20–25 minutes. The samples were quenched and the molecular weight distributions determined. The amounts of ingredients used, the temperature conditions and G.L.C. molecular weight distribution analyses are tabulated below wherein the Hal/Al ratio in each run was 3/1:

| Experiment Run | Grams Per 100 ml Monomer | | Reaction Temp. Range (° C) | Wt. % | | | | | | |
|---|---|---|---|---|---|---|---|---|---|---|
| | EASC | t-BuCl | | $C_8$ | $C_{16}$ | $C_{24}$ | $C_{32}$ | $C_{40}$ | $C_{48}$ | $C_{56}+$ |
| A | 0.5 | 1.5 | 95–124  | 4.8  | 7.08 | 14.7 | 16.4 | 17.1 | 13.7 | 26.5 |
| B | 1   | 3   | 102–113 | 1.0  | 7.75 | 12.2 | 16.7 | 16.4 | 13.3 | 32.4 |
| C | 2   | 6   | 97–109  | 2.42 | 7.68 | 10.0 | 14.8 | 15.6 | 16.6 | 33.4 |

The yield of oligomer in the $C_{24}$ to $C_{56}$ range for the runs were as follows: A, 88.1%; B, 91.3%; C, 89.9%. From the results shown above, it can be seen that while the yield of run A was lowest, this run had a lower average molecular weight and, as is known to those skilled in the art, thus had lower pour point than either runs B or C.

EXAMPLE VI

This example demonstrates the preparation of polyoctene on a much larger scale.

A dry twenty gallon jacketed steel autocalve reactor was steam heated to 256° F. under nitrogen. Two 8 gallon solvent storage bombs, with top and bottom access vents, were loaded as follows to provide an Hal/Al ratio of 3/1:

Bomb A — 50 pounds of octene-1 and 0.5 pound of ethyl aluminum sesquichloride

Bomb B — 50 pounds of octene-1 and 0.5 pound of tertiary butyl chloride.

The contents from bombs A and B were each fed at the rate of about 1.2 pounds/min. into the stirred reactor on which the heat had been turned off. Time, temperature and reactor pressure were recorded during the addition, which required 40 minutes. The reaction conditions are tabulated below:

| Reaction Time (min) | PSIG in Reactor | Internal Temp. (° C) | Jacket Temp. (Heat Off, ° C) |
|---|---|---|---|
| 0  | 0  | —     | 132 |
| 5  | 16 | 109   | —   |
| 10 | 26 | 132   | 137 |
| 15 | 25 | 141   | 137 |
| 20 | 26 | 140   | 137 |
| 25 | 28 | 135   | 137 |
| 30 | 31 | 133.7 | 137 |
| 33 | 32 | 133.7 | 137 |
| 40 | 37 | 133.7 | 137 |

At the end of 40 minutes, cooling water was circulated through the jacket for 10 minutes after which the reaction was shortstopped by the addition of 5 pounds of water. The reaction mixture was washed with 5% caustic solution (5% sodium hydroxide solution) and then again with water. The organic phase was separated and passed through a filtering column of activated alumina.

The whole oil obtained in this process had the following molecular weight distribution, as determined by G.L.C.

| | | Wt. % | | | | |
|---|---|---|---|---|---|---|
| $C_8$ | $C_{12} + C_{16} + C_{20}$ | $C_{24}$ | $C_{32}$ | $C_{40}$ | $C_{48}$ | $C_{56}+$ |
| 35 | 8.7 | 14.3 | 13.1 | 11.4 | 7.6 | 9.2 |

The whole oil was then subjeced to distillation whereby all hydrocarbons boiling below 150° C at 0.1 mm Hg. were removed resulting in a product yield of $C_{24}$ to $C_{56}$ of 56% having the following composition:

| | | Wt. % | | | |
|---|---|---|---|---|---|
| $<C_{24}$ | $C_{24}$ | $C_{32}$ | $C_{40}$ | $C_{48}$ | $C_{56}+$ |
| <1.0 | 21.8 | 23.2 | 21.8 | 13.1 | 19.2 |

The molecular weight of the product was calculated to be 538 and, when measured by osmometry, it was found to be 502.

This product oil had the following property charracteristics, wherein all kinematic viscosity values were obtained according to ASTM D445-64:

| | |
|---|---|
| Pour Point (ASTM D97-57) | $-75°$ F. |

| (Method B) | |
| --- | --- |
| Flash Point (ASTM D92-57) | 450° F. |
| Kinematic Viscosity at 100° F. | 32.7 cs. |
| Kinematic Viscosity at 210° F. | 5.6 cs. |
| Kinematic Viscosity at −40° F. | 8534 cs. |
| Kinematic Viscosity at −65° F. | 62500 cs. |
| Viscosity Index (ASTM D567-53) | 117 |

The above data clearly demonstrate that polyoctene oil having excellent properties can be attained in good conversion, using relatively small amounts of the novel soluble catalyst system and in very short reaction time.

The following examples were performed in equipment identical to that used in Example I above. Variations were made in the type of aluminum alkyl compound used, the wt. % of the aluminum alkyl compound, the Hal/Al ratio, and the temperature of reaction.

EXAMPLE VII

All of the following runs utilized 212 ml. of octene-1 (106 ml. in each addition funnel) and all were short-stopped after addition was completed in 30 minutes time. The resultant whole oils were analyzed by G.L.C. The yields were calculated as % ≧ $C_{24}$. The molecular weight figures correspond to product oil from which everything below $C_{24}$ has been separated by distillation. As mentioned earlier, ideally the yield of oligomer is to be maximized without the production of components higher than $C_{60}$.

The following table lists the reaction components and conditions for each run and illustrates the effect of changes in catalyst concentration, Hal/Al ratio, and reaction temperature on a series of oligomerizations in which octene solutions of $Et_3Al_2Cl_3$ (EASC) and benzyl chloride were mixed over a 30 minute period.

| Run No. | MMoles EASC | MMoles Benzyl Chloride | Wt. % EASC | Ratio Hal/Al | Reaction Temperature (° C) |
| --- | --- | --- | --- | --- | --- |
| 1. | 3 | 9 | 0.5 | 3/1 | 120 |
| 2. | 3 | 9 | 0.5 | 3/1 | 140 |
| 3. | 12 | 36 | 2.0 | 3/1 | 120 |
| 4. | 12 | 36 | 2.0 | 3/1 | 140 |
| 5. | 3 | 27 | 0.5 | 6/1 | 120 |
| 6. | 3 | 27 | 0.5 | 6/1 | 140 |

| | G.L.C. Analysis of Product Oils Obtained | | | | | | | | | |
| --- | --- | --- | --- | --- | --- | --- | --- | --- | --- | --- |
| Run | Wt. % | | | | | | | | | |
| No. | $C_8 + C_{12}$ | $C_{16}$ | $C_{20}$ | $C_{24}$ | $C_{32}$ | $C_{40}$ | $C_{48}$ | $C_{56}+$ | M.W.* | Yield (%) |
| 1. | 28.4 | 3.6 | 0.8 | 12.4 | 11.7 | 12.2 | 7.5 | 23.3 | 590 | 67.1 |
| 2. | 10.8 | 9.1 | 1.2 | 14.7 | 17.3 | 16.5 | 10.0 | 20.3 | 565 | 78.9 |
| 3. | 6.1 | 4.0 | 1.2 | 8.3 | 12.1 | 13.8 | 11.4 | 43.1 | 647 | 88.7 |
| 4. | 7.4 | 3.8 | 1.3 | 9.4 | 14.0 | 14.9 | 11.6 | 37.7 | 629 | 87.5 |
| 5. | 5.9 | 7.3 | 1.1 | 15.7 | 21.9 | 19.5 | 10.4 | 18.3 | 552 | 85.7 |
| 6. | 10.2 | 10.8 | 0.2 | 20.5 | 24.2 | 17.3 | 6.8 | 10.1 | 506 | 78.8 |

*Calculated average molecular weight of moieties of $C_{24}$ and higher.

The data tabulated above reveal that:

Runs performed at 140° C. produce lower molecular weight products than identical runs at 120° C. Thus, MW 1>2, 3>4, and 5>6.

Higher catalyst levels increase the molecular weight of the product oil in otherwise identical experiments. Thus, MW 3>1, and 4>2.

Higher Hal/Al ratios lower the molecular weight of the product oil. Thus, MW 1>5, and 2>6.

EXAMPLE VIII

The following runs illustrate the utility of ethyl aluminum dichloride (EADC) as the aluminum alkyl compound in the catalyst system of the invention. The reaction conditions and components used are tabulated below:

| Run No. | MMoles EADC | MMoles Benzyl Chloride | Wt.% EADC | Ratio Hal/Al | Reaction Temperature (° C.) | Reaction (Mixing) Time (Min.) |
| --- | --- | --- | --- | --- | --- | --- |
| 7. | 6 | 24 | 0.5 | 6/1 | 120 | 30 |
| 8. | 6 | 6 | 0.5 | 3/1 | 140 | 30 |

| | G.L.C. Analysis of Product Oils Obtained | | | | | | | | | |
| --- | --- | --- | --- | --- | --- | --- | --- | --- | --- | --- |
| Run | Wt. % | | | | | | | | | |
| No. | $C_8 + C_{12}$ | $C_{16}$ | $C_{20}$ | $C_{24}$ | $C_{32}$ | $C_{40}$ | $C_{48}$ | $C_{56}+$ | M.W. | Yield (%) |
| 7. | 7.1 | 5.2 | 1.0 | 12.3 | 18.2 | 17.7 | 12.3 | 26.2 | 588 | 86.7 |
| 8. | 27.8 | 4.8 | 0.6 | 13.7 | 12.9 | 12.0 | 7.6 | 20.6 | 574 | 67.0 |

EXAMPLE IX

This example, carried out in the same way as Example VIII above, illustrates the use of diethyl aluminum chloride (DEAC) as the aluminum alkyl compound in the catalyst system of the invention, the details being tabulated below:

| MMoles DEAC | MMoles Benzyl Chloride | Wt.% DEAC | Ratio Hal/Al | Reaction Temp. (° C) | Reacting (Mixing) Time (min.) |
| --- | --- | --- | --- | --- | --- |
| 6 | 12 | 0.5 | 3/1 | 140 | 30 |

| G.L.C. Analysis of Product Oil Obtained | | | | | | | | | |
| --- | --- | --- | --- | --- | --- | --- | --- | --- | --- |
| Wt. % | | | | | | | | | |
| $C_8 + C_{12}$ | $C_{16}$ | $C_{20}$ | $C_{24}$ | $C_{32}$ | $C_{40}$ | $C_{48}$ | $C_{56}+$ | M.W. | Yield (%) |

-continued

| 11.0 | 11.3 | 1.1 | 19.4 | 20.6 | 15.2 | 7.8 | 13.5 | 525 | 76.5 |

EXAMPLE X

This example illustrates the preparation of polydecene by the process of the invention on a large scale. The apparatus used was the same as described in Example VI above.

A dry 20 gallon jacketed steel autoclave reactor was steam heated to 140° C. Two 8 gallon solvent bombs, A and B, with top and bottom access vents were loaded as follows:

Bomb A: 50 pounds of decene-1 and 0.5 pound of $Et_3Al_2Cl_3$ (EASC) (as 2 pounds of a 25% hexane solution).

Bomb B: 50 pounds of decene-1 and 3 pounds of allyl chloride.

Hal/Al ratio: 16/1

The contents from bombs A and B were each fed at the rate of one pound/minute into the stirred reactor. After 25 minutes, the internal temperature had reached 152° C and the external heating was turned off. Fifty minutes were required for addition of both A and B contents. At the end of this time, the internal pressure was 27.5 PSIG and the internal temperature was 156° C.

At this point, cooling water was circulated through the reactor jacket for ten minutes after which the reaction was shortstopped by the addition of 5 pounds of water. The reaction mixture was washed with 5% caustic solution (5% sodium hydroxide solution) and then again with water.

The whole oil obtained in this process had the following molecular weight distribution as determined by G.L.C. analysis:

| | | | Wt. % | | | | |
|---|---|---|---|---|---|---|---|
| $C_{10}$ | $C_{13}$ | $C_{20}$ | $C_{23}$ | $C_{30}$ | $C_{40}$ | $C_{50}$ | $C_{60}+$ |
| 10.6 | 4.4 | 20 | 0 | 24.6 | 20.4 | 10.7 | 8.9 |

The yield of product $\geq C_{20}$ was 85%.

The whole oil was then distilled under reduced pressure to remove all hydrocarbons below $C_{20}$. G.L.C. analysis of the resulting product oil showed the following:

| | Wt. % | | | |
|---|---|---|---|---|
| $C_{20}$ | $C_{30}$ | $C_{40}$ | $C_{50}$ | $C_{60}+$ |
| 21.7 | 28.2 | 23.9 | 12.9 | 12.8 |

This product oil had the following property characteristics:

| | |
|---|---|
| Pour Point (ASTM D97-57) | −80° F |
| Kinematic Viscosity at 100° F (ASTM D445-64) | 26.4 cs |
| Kinematic Viscosity at 210° F. (ASTM D445-64) | 4.9 cs |
| Viscosity Index (ASTM D567-53) | 123 |
| Average M.W. by osmometry | 472 |

EXAMPLE XI

This example was carried out in the same manner as Example X above to illustrate how good yields and higher molecular weights are attainable by increasing the amount of aluminum alkyl compound and lowering the Hal/Al ratio to 4/1.

In this example, bomb A contained 50 pounds of decene-1 and one pound of $Et_3Al_2Cl_3$ (EASC). (As 4 pounds of a 25% hexane solution).

Bomb B contained 1.5 pounds of allyl chloride dissolved in 50 pounds of decene-1.

The reactants were mixed over a 30 minute period in the 20 gallon autoclave which had been preheated to 140° C. The maximum temperature attained was 167° C. and the internal pressure reached 30 PSIG.

Cooling water was then circulated for ten minutes, following which the solution was shortstopped and washed. The whole oil obtained had the following molecular weight distribution as determined by G.L.C. analysis:

| | | | Wt. % | | | | |
|---|---|---|---|---|---|---|---|
| $C_{10}$ | $C_{13}$ | $C_{20}$ | $C_{23}$ | $C_{30}$ | $C_{40}$ | $C_{50}$ | $C_{60}+$ |
| 6.6 | 2.2 | 17.1 | 0 | 22.8 | 23.1 | 12.7 | 15.6 |

The product yield of $\geq C_{20}$ was 91.2%.

The oil was distilled under reduced pressure to remove all hydrocarbons below $C_{20}$. G.L.C. analysis of the resulting product oil showed the following composition:

| | Wt. % | | | |
|---|---|---|---|---|
| $C_{20}$ | $C_{30}$ | $C_{40}$ | $C_{50}$ | $C_{60}+$ |
| 19 | 24 | 24.3 | 14.3 | 17.6 |

The product oil had the following property characteristics:

| | |
|---|---|
| Pour point (ASTM D97-57) | −70° F. |
| Kinematic Viscosity at 100° F. (ASTM D445-64) | 31.2 cs |
| Kinematic Viscosity at 210° F. (ASTM D445-64) | 5.5 cs |
| Viscosity Index (ASTM D567-53) | 124 |
| Average M. W. by osmometry | 490 |

EXAMPLE XII

A mixture (ca 2/1) of $C_{16}$ and $C_{24}$ olefins (100g), which was distilled off from a previously prepared oil derived from octene-1, was treated with 50 grams of bromine at room temperature over the course of an hour. After the addition was complete, the red oily product was washed with aqueous base, the layers separated and the organic layer dried. The resultant halogenated product weighed 135 grams and contained 26 % bromine. This alkyl bromide is used below as the cocatalyst with ethyl aluminum sesquichloride for the oligomerization of octene-1.

A 3-necked round bottom flask, fitted with 2 Y tubes into which were mounted a stirrer, thermometer, an $N_2$ inlet and 2 dropping funnels (125 ml), was placed in an oil bath heated to 120° C. In one of the dropping funnels was placed 106 ml (76.5g) octene-1 and 4 ml of 25% ethyl aluminum sesquichloride. In the other dropping funnel was placed 10 grams of the above-prepared alkyl bromide so that the hal/al ratio was 8/1 and 96 ml (69.2g) octene-1. A head of nitrogen was kept over the contents of each funnel during the entire reaction:

The contents of both dropping funnels were added simultaneously to the stirred heated flask at such a rate as to require 30 minutes for the complete addition of both. During this time, the temperature in the flask reached 125° C, only slightly warmer than the surrounding bath temperature. After addition was complete, the reaction was stirred for an additional 5 minutes and was then quenched by the addition of 100 ml of 5% NaOH (aqueous). The organic layer was then separated, dried and analyzed for its molecular weight distribution:

The molecular weight distribution of the product was, in weight percent:

| $C_8$ | $C_8+$ | $C_{16}$ | $C_{16}+$ | $C_{24}$ | $C_{32}$ | $C_{40}$ | $C_{48}$ | $C_{56}+$ |
|---|---|---|---|---|---|---|---|---|
| 6.2 | 2.0 | 7.1 | 1.4 | 15.0 | 21 | 20.2 | 16.6 | 10.4 |

This corresponds to an 83% yield of oil having m.w $\geq$ $C_{24}$.

In a similar experiment, 20 grams of the alkyl bromide of above was utilized as cocatalyst such that the hal/al ratio was 14/1. The above procedure was repeated and the resultant product had the following molecular weight distribution in weight percent:

| $C_8$ | $C_8+$ | $C_{16}$ | $C_{16}+$ | $C_{24}$ | $C_{32}$ | $C_{40}$ | $C_{48}$ | $C_{56}+$ |
|---|---|---|---|---|---|---|---|---|
| 5.9 | 4.1 | 9.9 | 1.8 | 20.2 | 22.4 | 18.2 | 13.1 | 4.7 |

This corresponds to a yield of 78.7% of oil having molecular weight $\geq C_{24}$.

EXAMPLE XIII

The following example illustrates the variety of organo halides which are operable as cocatalysts with the alkyl aluminum halides in the present invention.

The examples are run as previous examples, employing 2 dropping funnels, one containing 106 (76.5g) octene-1 and 4 ml of 25% EASC and the other containing 106 ml octene-1 and the specified amount of alkyl halide. The reaction temperature is 120° C and the time of addition is 30 minutes.

| | Organo Halide, | g | Hal/al Ratio | Halide formula |
|---|---|---|---|---|
| (a) | Cyclohexyl bromide, | 1.45 | 3/1 | $C_6H_{11}Br$ |
| (b) | Dodecyl iodide, | 3.17 | 3/1 | $C_{12}H_{25}I$ |
| (c) | 1-chloro eicosane | 2.85 | 3/1 | $C_{20}H_{41}Cl$ |
| (d) | 2-chloro eicosane | 2.85 | 3/1 | " |
| (e) | 1,2-dibromo hexadecane | 1.65 | 3/1 | $C_{16}H_{32}Br_2$ |
| (f) | dodecyl benzyl chloride | 3.55 | 3/1 | $C_{19}H_{31}Cl$ |

In all cases above, the resultant oil is obtained having at least 70% of the olegomer as an oil $\geq C_{24}$. This example illustrates that the structure, molecular weight and choice of halogen of the organo halide has little effect on its efficiency as a cocatalyst in the method.

While the invention has been described with particularity and in some detail, it will be recognized by those skilled in the art that various changes and modifications can be made therein without departing from the scope and spirit of the invention.

What is claimed is:

1. A method of oligomerizing straight chain alpha olefins having at least 3 carbon atoms comprising, generating in situ a soluble catalyst system by simultaneously adding with stirring to a reactor having an inert atmosphere and a temperature up to 200° C., a first feed comprising a straight chain alpha-olefin monomer having at least 3 carbon atoms and a minor amount of a soluble aluminum alkyl halide and a second feed comprising a straight chain alpha-olefin monomer having at least three carbon atoms and a minor amount of a soluble organic halide; wherein said soluble aluminum alkyl halide compound is selected from the group consisting of ethyl aluminum sesqui-chloride, ethyl aluminum dichloride and diethyl aluminum chloride, and said soluble organic halide is selected from the group consisting of a primary, secondary or tertiary aliphatic halide, an allylic halide or a benzylic halide, said soluble organic halide possessing; (a) at least one halogen-bearing carbon atom in the molecule and (b) not more than one halogen atom attached to any single carbon atom in said molecule; said aluminum alkyl halide being present in said catalyst system in an amount of at least about 0.1% by weight of the total monomer content and in sufficient amount to provide a total Hal/Al ratio in said catalyst system of at least about 2.5/1.

2. The method of claim 1 wherein said straight chain alpha-olefin is a member seleced from the group consisting of propene, butene, pentene, hexene, heptene, octene, nonene, decene, undecene, dodecene, tridecene, and tetradecene; said organo halide is a member selected from the group consisting of t-butyl chloride, allyl chloride, benzyl chloride and a mixture of halogenated $C_{24}$ of an below oligomers and alpha-olefin; and, said temperature is at least about 100° C.

3. The method of claim 1 wherein products having a molecular weight of less than about 280 are removed by vacuum distillation.

4. The method of claim 3 wherein the products removed are halogenated and then recycled as the organo halide compound.

5. The method of claim 1 wherein the yield of oligomer obtained is at least about 56% based upon the weight of said straight chain alpha-olefins, and the average molecular weight of said oligomer is at least about 280.

6. The method of claim 1 wherein said straight chain alpha-olefin is octene-1.

7. The method of claim 1 wherein said straight chain alpha-olefin is decene-1.

8. The method of claim 1 wherein the reaction temperature is between 23° C and 200° C.

9. The method of claim 1 wherein said straight chain alpha-olefin is a mixture of octene-1 and decene-1.

* * * * *